US00PP11017P

United States Patent [19]

Chamberlin, Sr.

[11] Patent Number: Plant 11,017

[45] Date of Patent: Jul. 27, 1999

[54] PEACH TREE NAMED '92-287'

[75] Inventor: Thomas O. Chamberlin, Sr., Visalia, Calif.

[73] Assignee: Corrin Family Trust, Reedly, Calif.

[21] Appl. No.: 08/988,171

[22] Filed: Dec. 10, 1997

[51] Int. Cl.[6] ..... A01H 5/00

[52] U.S. Cl. ..... Plt./198

[58] Field of Search ..... Plt./43.2, 198

*Primary Examiner*—Howard J. Locker
*Assistant Examiner*—Anne Marie Grünberg
*Attorney, Agent, or Firm*—Richard A. Ryan

[57] ABSTRACT

A new and distinct variety of peach tree which is distinguished by producing free stone fruit which are mature for harvesting and shipment approximately September 10 to September 15 in the San Joaquin Valley of central California. The fruit are large, round and very firm and do not bruise easily. The flesh is crisp with a clear yellow coloration.

1 Drawing Sheet

BACKGROUND OF THE NEW VARIETY

The present invention relates to a new and distinct variety of peach tree, which will hereinafter be denominated varietally as the '92-287' peach tree, and, more particularly, to such a peach tree which produces free stone fruit having clear yellow flesh and red pit cavity which mature for commercial harvesting and shipment approximately September 10 to September 15 in the San Joaquin Valley of central California.

Although the varieties of peach trees producing commercially acceptable fruit relatively common, it is not common to find peach varieties that produce commercially acceptable fruit at the beginning or end of the typical peach growing season. Most peaches available at the end of the growing season are usually characterized as only marginally acceptable due to various factors, including poor coloration or taste, small size and unsuitable handling abilities. New peach varieties which produce fruit at the end of the growing season that have characteristics which are found in fruit produced at or near the peak portion of the growing season are usually considered to be commercially valuable. The variety of peach tree of the present invention is such a variety, as set forth herein.

ORIGIN AND ASEXUAL REPRODUCTION OF THE NEW VARIETY

The peach tree of the present invention was discovered by the inventor as a chance seedling in a nursery located near Reedley in the San Joaquin Valley of central California. The first fruit was seen on this seedling in September of 1992. As the fruit matured, it was examined as to size, shape, coloration, ripening date, flavor, texture and as to other criteria which were sought in a peach variety having the desired commercial potential. The initial fruit had the size, shape, color and handling characteristics which the inventor was looking for in the early to mid-September date period. Specifically, the fruit was a free stone peach having clear yellow flesh and was very firm, making it easy to handle and able to ship well. The seedling was marked for further testing.

Bud wood was collected from this seedling in the Winter of 1992-1993. Seedlings were grafted onto Nenaguard rootstock in the early Spring of 1993 in the testing part of the nursery. Additional seedlings were grafted in the early Spring of 1994. The first fruit from these asexually produced trees of the new variety was observed by the inventor in September 1995.

The harvest time for the asexually produced trees of this new variety was early to mid-September, the same time as the original seedling. These trees produced the same large, round fruit having flesh of a very firm texture as that seen on the original seedling. The flavor of the fruit was very good. The flesh coloration of the fruit was the same clear yellow color. The leaves and bark matched those on the original seedling. The inventor has confirmed that the asexually reproduced trees of the new variety are the same in all respects to the original seedling.

SUMMARY OF THE NEW VARIETY

'92-287' peach tree is characterized by producing a fruit which has a yellow flesh coloration and is ripe for harvesting and shipment approximately September 10 to September 15 in the San Joaquin Valley of central California. The fruit of the new variety are approximately three (3) inches or larger in diameter and almost fully round in shape. The flavor of the fruit at harvest date is good. The fruit is crisp, but it still has good flavor. The skin of the fruit from this variety is very high color, almost full red. The flesh is full yellow with red only in the pit cavity. At harvest time this fruit is very firm, making it easy to handle and ship. The skin is tenacious to the flesh, which also helps in handling and shipping. The inventor has not seen any breakdown on the suture line, or at the base or apex area of this fruit. The fruit has been determined to have outstanding storage life, retaining its firm flesh of very good flavor even after thirty (30) days in cold storage. The inventor has kept fruit from this new variety on the shelf for a week at room temperature and it held up very well.

BRIEF DESCRIPTION OF THE DRAWING

The drawing is a color photograph showing mature fruit of the new variety including a first in top plan view showing the base thereof; a second in side elevation showing the suture thereof; a third sectioned and laid open to show the stone in one section and the stone cavity in the other section; a fourth in side elevation; a fifth in bottom plan view showing the apex area thereof; and representative foliage, all of the new variety.

DETAILED DESCRIPTION

Referring more specifically to the pomological details of this new and distinct variety of peach tree, the following has been observed under the ecological conditions prevailing at the orchard of origin, which is located near Reedley, Calif.

All major color code designations are by reference to the *Inter-Society Color Council, National Bureau of Standards* color name chart. Common color names are also occasionally employed.

TREE

Generally:
- *Size.*—Normal as to pruning and shaping. In first year, four to five feet in height and three feet wide on a single leader tree.
- *Vigor.*—Very vigorous, spring growth three to four feet in length.
- *Productivity.*—Very good, 36 pounds per tree.
- *Regularity of bearing.*—Will bear well every year.

Trunk:
- *Size.*—Normal diameter.
- *Surface Texture.*—Normal peach tree bark.
- *Color.*—72 d.oy.
- *Lenticels—numbers.*—Approximately 22 small lenticels per square inch
- *Lenticels —size.*—Approximately 0.318 cm (⅛ inch) long.

Trunk:
- *Size.*—Normal diameter.
- *Surface texture.*—Normal peach tree bark.
- *Color.*—72 d.oy.
- *Lenticels —numbers.*—Approximately 22 small lenticels per square inch.
- *Lenticels —size.*—Approximately 0.318 cm (⅛ inch) long.
- *Bark color.*—Light grey brown (80 gr.y.Br).

Branches:
- *Size.*—Normal as to pruning and shaping.
- *Surface texture.*—Normal. Same characteristics as the trunk.
- *Surface color.*—Light grey brown (80 gr.y.Br.).
- *Lenticels —size —length.*—About 20-22 per square inch. Approximately 0.318 cm (⅛ inch) in length.
- *Color.*—72 d.oy

LEAVES

Size:
- *Generally.*—Normal
- *Average length.*—13.97 cm (1½ inches) to 17.78 (7 inches).
- *Average width.*—2.54 cm (1 inch) to 3.175 cm (1¼ inches).
- *Leaf thickness.*—Normal.

Shape: Lanceolate.

Color:
- *Upwardly disposed surface.*—Dark green. (125 m.ol.G).
- *Downwardly disposed surface.*—Lighter green (120 m.Y.G).

Marginal form: Serrate.

Petiole:
- *Length.*—1.27 cm (½ inch).
- *Width.*—0.159 cm (1/16 inch).

Stem glands:
- *Number.*—Will vary. 1–2 pair per leaf stem.
- *Arrangement.*—Found in pairs on each side of petiole of leaf base.
- *Size.*—Very small depending on age and size of leaf.
- *Type.*—Reniform.
- *Color.*—Light yellow. (73 p.oy).

FLOWER BUDS

Generally: Information taken as color starting to shown at apex of bud.
- *Size —Length.*—0.438 cm (7/16 inch).
- *Size —diameter.*—0.313 cm (5/16 inch).
- *Shape.*—Slightly elongated. Bud looks round in appearance.
- *Petiole.*—Very short approximately 0.159 cm (1/16 inch).
- *Color.*—Very dark red brown. (17 V.d.Red).
- *Other characteristics.*—Dark red bud with bright pink showing at apex (2 S.pink).

FLOWERS

Date of bloom: Approximately February 27$^{th}$ to March 8$^{th}$ at Reedley, Calif.

Petals:
- *Diameter.*—1.746 cm (11/16 inch).
- *Length.*—2.064 cm (13/16 inch).
- *Shape of each petal.*—Slightly elongated.
- *Bloom —diameter.*—5.08 cm (2 inches).
- *Fragrance.*—No characteristic fagrance.

Color: Bright pink (4.1-pink) with darker pink at base (2S. pink).

Fertility: Self fertile.

Petiole length: Very short, approximately 0.159 cm (1/16 inch).

Other characteristics: Large light pink blossoms.

FRUIT

Date of maturity: Approximately September 10$^{th}$ to 15$^{th}$ at Reedley, Calif.

Size:
- *Generally.*—Large and uniform.
- *Uniformity.*—Very good. Very round with medium to wide base and round apex area.
- *Diameter.*—Aproximately 6.985 cm (2¾ inches) to 8.255 cm (3¼ inches).
- *Transverse in suture plane.*—Approximately 8.255 cm (3¼ inches) to 9.535 cm (3¾ inches).
- *Transverse at right angle to suture plane.*—6.985 cm (2¾ inches) to 8.255 cm (3¼ inches).
- *Symmetrical.*—Yes.

Suture:
- *Generally.*—Mostly very smooth.
- *Length.*—From base to apex 11.43 cm (4½ inches) to 12.7 cm (5 inches).

Stem cavity: Rounded approximately 1.27 cm (½ inch) deep.

Base: Medium wide and rounded.

Apex area: Slightly rounded.

Pistil point: Very small.

Stem:
- *Size. —length.*—Approximately 1.27 cm (½ inch).
- *Size. —diameter.*—Approximately 0.188 cm (3/16 inch).

Skin:
- *Thickness.*—Normal peach skin.
- *Texture.*—Smooth and tenacious to flesh.
- *Color.*—Dark red with some bright yellow. (a) Dark red (17 V.d.Red), 50 % on exposed portion. (b) Bright Red (13 Deep red), 40 % on reversed portion. (c) Yellow (68 S.oy.), 10% background color on least exposed portion.
- *Tendency to crack.*—None.
- *Pubescence.*—Very light.

*Weight.—Average* 3per pound.
*Sugar content.*—18 Brix.

Flesh:
*Color.*—Yellow. (83 brill Y.).
*Surface of pit cavity.*—Rough and dark red in color (13 Deep red).
*Juice production.*—Medium juicy.
*Aroma.*—Slight.
*Fibers.*—None.
*Flavor.*—Mild. Low acid.
*Ripening.*—Even.
*Eating quality.*—Has mild flavor. Very low acid taste. Will be quite crisp at harvest date.

Stone:
*Attachment.*—Free.
*Fibers.*—None.
*Size —length.*—3.969 cm (1 9/16 inches).
*Size —width.*—2.54 cm (1 inch).
*Size —thickness.*—1.905 cm (3/4 inch).
*Color —dry.*—Dark red. (41 Deep r.Br).
*Form.*—Ovid.
*Base —shape.*—Elongated.
*Base —length.*—0.794 cm (5/16 inch).
*Base —width.*—0.635 cm (1/4 inch).
*Apex —shape.*—Pointed.
*Sides —generally.*—Rough.
*Ridges.*—Some approximately 0.079 cm (1/32 inch) to 0.063 cm (1/16 inch) deep.
*Tendency to split.*—None.

Use: Fresh Market.

Keeping quality: Very good shelf life. Kept at room temperature for about one week. Has kept in cold storage for over 30 days.

Shipping and handling quality: Due to firm nature of fruit, it will ship and handle very well.

Although the new variety of peach tree possesses the described characteristics noted above as a result of the growing conditions prevailing near and in the central part of the San Joaquin Valley of California, it is to be understood that variations in the usual magnitude and characteristics incident to changes in growing conditions, irrigation, fertilization, pruning, pest control, climatic variation and the like are to be expected.

Having thus described an illustrated my new variety of peach tree, what I claim as new and desire to be secured by Plant Letters Patent is:

1. A new and distinct variety of peach tree substantially as illustrated and described which is distinguished by producing large, fully rounded free stone fruit having clear yellow flesh coloration that is crisp and firm and which are mature for commercial harvesting and shipment approximately September 10 to September 15 in the San Joaquin Valley of central California.

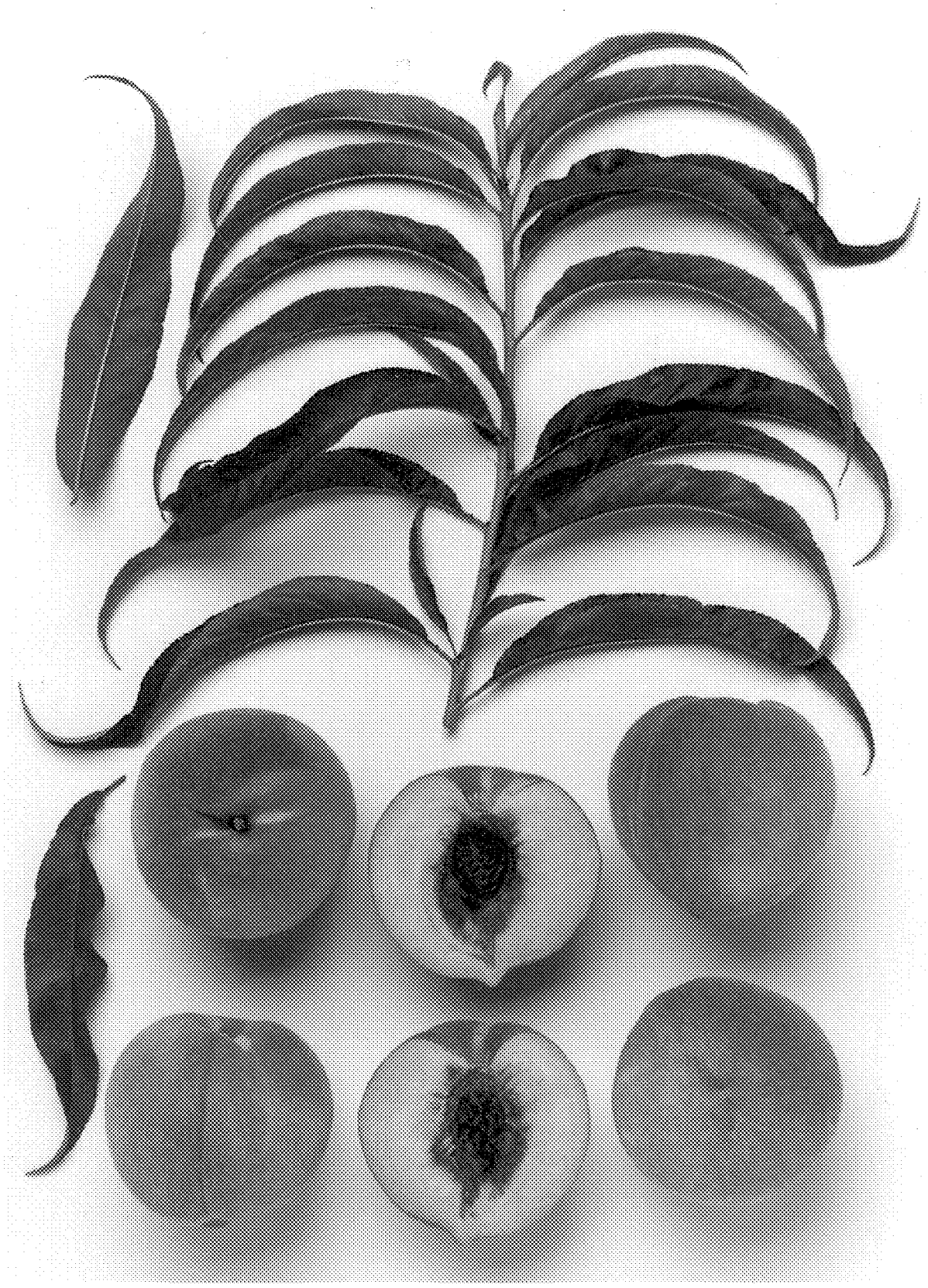

* * * * *